United States Patent [19]

Orita et al.

[11] Patent Number: 4,952,712
[45] Date of Patent: Aug. 28, 1990

[54] PROCESS FOR THE PREPARATION OF 2,3-DIMETHOXY-5-METHYLBENZOQUINONE

[75] Inventors: Hideo Orita; Masao Shimizu; Takashi Hayakawa; Katsuomi Takehira, all of Tsukuba, Japan

[73] Assignee: Director-General of Agency of Industrial Science and Technology, Japan

[21] Appl. No.: 322,416

[22] Filed: Mar. 13, 1989

[30] Foreign Application Priority Data

Jun. 13, 1988 [JP] Japan .................................. 63-145099

[51] Int. Cl.$^5$ ....................... C07C 46/10; C07C 66/00
[52] U.S. Cl. .................................................. 552/307
[58] Field of Search ...................... 260/396 R; 552/307

[56] References Cited

U.S. PATENT DOCUMENTS 4,482,493 11/1984 Matsumoto et al. ............ 260/396 R

OTHER PUBLICATIONS

Korenskii et al., Zh. Obshch. Khim. 55, pp. 1969–1975, Sep., 1985.

*Primary Examiner*—Paul J. Killos
*Attorney, Agent, or Firm*—Lorusso & Loud

[57] ABSTRACT

2,3-Dimethoxy-5-methylbenzoquinone is prepared by oxidizing 3,4,5-trimethoxytoluene by reaction with hydrogen peroxide in the presence of a catalyst which is a heteropolyacid selected from phosphomolybdic acids, phosphotungstic acids, silicomolybdic acids and silicotungstic acids or a salt thereof.

11 Claims, No Drawings

PROCESS FOR THE PREPARATION OF 2,3-DIMETHOXY-5-METHYLBENZOQUINONE

BACKGROUND OF THE INVENTION

1. Field of the Invention:

This invention relates generally to a process for the preparation of 2,3-dimethoxy-5-methylbenzoquinone and, more specifically, to a one-stage process for the production of 2,3-dimethoxy-5-methylbenzoquinone by oxidation of 3,4,5trimethoxytoluene with hydrogen peroxide using, as a catalyst, a heteropolyacid containing molybdenum or tungsten and phosphorus or silicon as two heteronucleus metal elements thereof.

2. Description of the Prior Art 2,3-Dimethoxy-5-methylbenzoquinone is an important intermediate compound for a quinone-type antitumor agent or a coenzyme Q. One known method of preparing 2,3-dimethoxy-5-methylbenzoquinone includes coupling 3,4,5-trimethoxytoluene with a p-nitrobenzenediazonium salt to form an azo compound, reducing the azo compound to form an o-toluidine derivative, and oxidizing the o-toluidine derivative (Japanese Examined Patent Publication No. 38-11,981). This process is, however, low in efficiency because of its multi-step process and requires a large amount of an oxidizing agent, leading to the production of a large amount of industrial waste as a by-product.

One well known one stage process for the production of 2,3-dimethoxy-5-methylbenzoquinone includes oxidizing 3,4,5-trimethoxytoluene using a hexacyanoferrate as a catalyst (J. Org. Chem., 50, 1766 (1985)). This process has a problem that the catalyst contains highly toxic cyano ions. Furthermore, the yield of the benzoquinone with this process is not satisfactory.

SUMMARY OF THE INVENTION

In accordance with the present invention there is provided a process for the preparation of 2,3-dimethoxy-5methylbenzoquinone, comprising reacting 3,4,5-trimethoxytoluene with hydrogen peroxide in the presence of a heteropolyacid selected from the group consisting of phosphomolybdic acids, phosphotungstic acids, silicomolybdic acids and silicotungstic acids or a salt thereof.

As a result of an extensive study on oxidizing catalysts for the preparation of 2,3-dimethoxy-5methylbenzoquinone, it has been found that a heteropolyacid or its salt containing Mo or W and P or Si as its heteronucleus metal ions can produce with a high yield the desired benzoquinone when used as a catalyst for the oxidation of 3,4,5trimethoxytoluene and that commercially easily available hydrogen peroxide is effectively used as the oxidation agent in conjunction with such a heteropolyacid catalyst.

In the process according to the present invention, since hydrogen peroxide used as the oxidizing agent is converted into water, no dangerous waste materials are produced. Further, the process of the present invention is advantageous from the standpoint of economy because the oxidation is carried out at a temperature not higher than 100° C, and because the starting materials are commercially available at low prices.

It is an object of the present invention to provide a process which can convert 3,4,5-trimethoxytoluene into 2,3-dimethoxy-5-methylbenzoquinone with a high yield in an economical manner.

Another object of the present invention is to provide a process of the above-mentioned type which is free of causing industrial pollution.

Other objects, features and advantages of the present invention will become apparent from the detailed description of the invention to follow.

DETAILED DESCRIPTION OF THE INVENTION

The present invention provides a process for the preparation of 2,3-dimethoxy-5-methylbenzoquinone, in which 3,4,5-trimethoxytoluene is reacted with hydrogen peroxide in the presence of a heteropolyacid selected from the group consisting of phosphomolybdic acids, phosphotungstic acids, silicomolybdic acids and silicotungstic acids or a salt thereof.

Hydrogen peroxide to be used as an oxidizing agent may be an aqueous hydrogen peroxide having various concentrations. A commercially available 30 % aqueous hydrogen peroxide may be suitably used. More highly concentrated hydrogen peroxide solutions, for example those having a 50–60 % concentration may also be used, if desired. The amount of hydrogen peroxide to be used for the oxidation of the 3,4,5-trimethoxytoluene may be suitably determined in accordance with an optimum yield and is generally in the range of from 1–30 times the stoichiometric amount, preferably 2–10 times the stoichiometric amount.

The phosphorus ions of the phosphomolybdic acids and phosphotungstic acids may be both trivalent and pentavalent ions. Both ortho- and iso-silicomolybdic or silicotungstric acids may be used for the purpose of the present invention. Illustrative of suitable heteropolyacids are $H_3PMo_{12}O_{40}$, $H_3PW_{12}O_{40}$, $H_3PMo_6W_6O_{40}$, $H_4SiMo_{12}O_{40}$ and $H_4SiW_{12}O_{40}$.

Salts of the above heteropolyacids, such as alkali metal salts and ammonium slats, may also be used. Examples of suitable alkali metals include lithium, potassium and sodium. The heteropolyacid is used in a catalytically effective amount, preferably 0.0001–0.05 mole, more preferably 0.001–0.03 mole per mole of the starting material 3,4,5-trimethoxytoluene.

The oxidation is preferably carried out using a solvent. Since hydrogen peroxide is used as an oxidizing agent, the solvent to be used is preferably a water-soluble organic solvent so as to provide a homogeneous reaction system. Illustrative of suitable water-soluble organic solvents are organic acids such as formic acid, acetic acid, propionic acid, acid anhydrides such as acetic anhydride, a lower alcohol such as methanol and ethanol, ketones such as acetone, and other solvents such as acetonitrile and N,N-dimethylformamide. Above all, the use of an organic acid is especially preferred.

The reaction temperature to be used in the process of the present invention does not require a particularly strict control and generally ranges from 0° C. to 100° C., preferably from 10° C. to 70° C. The reaction time varies with the concentration of hydrogen peroxide and the amount of the catalyst used but generally ranges from 1 to 24 hours.

The color of the reaction solution turns orange as the reaction proceeds. After completion of the reaction, water is added to the reaction mixture and the resulting mixture is extracted with a water-insoluble organic solvent. The extract is dried over magnesium sulfate and is subjected to distillation, thereby to leave 2,3-dimethoxy-5-methylbenzoquinone.

In accordance with the present invention, 2,3-dimethoxy-5-methylbenzoquinone can be prepared in one step from 3,4,5-trimethoxytoluene with a high yield. Furthermore, the method of the present invention does not produce undesirable industrial wastes.

The following examples will further illustrate the present invention.

EXAMPLES 1–4

In a glass flask was placed a solution of 2 mmol of 3,4,5-trimethoxytoluene and 100 mg of a heteropolyacid as indicated in Table 1 below in 10 ml of acetic acid. To this solution was dropwise added 2 ml of a 31% aqueous hydrogen peroxide solution. The mixture was stirred at 30° C. for 5 hours in a nitrogen atmosphere. After completion of the reaction, 50 ml of water was added and the mixture was extracted three times with a 20 ml portion of methylene chloride. The extract was dried over magnesium sulfate and subjected to distillation for the removal of the solvent. The resultant product was confirmed to be 2,3-dimethoxy-5-methylbenzoquinone by NMR spectroscopy. The yield of the product was determined by gas chromatography. The results are summarized in Table 1.

TABLE 1

| Examples | Heteropoly Acids | Conversion (%) | Yield (%) | Selectivity (%) |
|---|---|---|---|---|
| 1 | Phosphomolybdic acid | 81 | 32 | 40 |
| 2 | Silicomolybdic acid | 68 | 23 | 34 |
| 3 | Phosphotungstic acid | 57 | 23 | 40 |
| 4 | Silicotungstic acid | 69 | 23 | 33 |

EXAMPLE 5

The procedures of Example 1 were followed with the exception that the reaction time was 7 hours and 1 ml of the 31% aqueous peroxide solution was used. The results are shown in Table 2 below.

TABLE 2

| Examples | Heteropoly Acids | Conversion (%) | Yield (%) | Selectivity (%) |
|---|---|---|---|---|
| 5 | Phosphomolybdic acid | 89 | 49 | 55 |

EXAMPLES 6–7

The procedures of Examples 1 and 2 were followed with the exception that 50 mg of the heteropoly acid as shown below was used and the reaction time was 14.5 hours. The results are shown in Table 3 below.

TABLE 3

| Examples | Heteropoly Acids | Conversion (%) | Yield (%) | Selectivity (%) |
|---|---|---|---|---|
| 6 | Phosphomolybdic acid | 97 | 50 | 52 |
| 7 | Silicomolybdic acid | 95 | 52 | 55 |

EXAMPLES 8–9

The procedures of Examples 1 and 2 were followed with the exception that 200 mg of the heteropoly acid as shown below and 4 mmol of 3,4,5-trimethoxytoluene were used. The results are shown in Table 4 below.

TABLE 4

| Examples | Heteropoly Acids | Conversion (%) | Yield (%) | Selectivity (%) |
|---|---|---|---|---|
| 8 | Phosphomolybdic acid | 75 | 55 | 73 |
| 9 | Silicomolybdic acid | 77 | 51 | 66 |

EXAMPLE 10

The procedures of Example 1 were followed with the exception that 4 mmol of 3,4,5-trimethoxytoluene and 50 mg of phosphotungstomolybdic acid ($H_3PMo_6W_6O_{40}$) were used, and the reaction time was 15.5 hours. The results are shown in Table 5 below.

TABLE 5

| Example | Conversion (%) | Yield (%) | Selectivity (%) |
|---|---|---|---|
| 10 | 94 | 51 | 54 |

EXAMPLES 11–12

The procedures of Examples 1 and 2 were followed with the exception that 200 mg of the heteropoly acid as shown below and 4 mmol of 3,4,5-trimethoxytoluene were used, and the reaction temperature was 40° C. The results are shown in Table 6 below.

TABLE 6

| Examples | Heteropoly Acids | Conversion (%) | Yield (%) | Selectivity (%) |
|---|---|---|---|---|
| 11 | Phosphomolybdic acid | 99 | 39 | 39 |
| 12 | Silicomolybdic acid | 98 | 34 | 35 |

EXAMPLES 13–14

The procedures of Examples 1 and 2 were followed with the exception that 20 mg of the heteropoly acid as shown below, 4 mmol of 3,4,5-trimethoxytoluene, 1 ml of the 31% aqueous hydrogen peroxide solution and 10 ml of formic acid as a solvent were used, and the reaction time was 1 hour. The results are shown in Table 7 below.

TABLE 7

| Examples | Heteropoly Acids | Conversion (%) | Yield (%) | Selectivity (%) |
|---|---|---|---|---|
| 13 | Phosphomolybdic acid | 96 | 57 | 59 |
| 14 | Silicomolybdic acid | 95 | 56 | 59 |

COMPARATIVE EXAMPLE 1

The procedures of Example 1 were followed without use of phosphomolybdic acid as the catalyst. The results are shown in Table 8 below.

TABLE 8

| Compara. Example | Conversion (%) | Yield (%) | Selectivity (%) |
|---|---|---|---|
| 1 | 40 | 4 | 10 |

COMPARATIVE EXAMPLE 2

The procedures of Example 1 were followed with the exception that 50 mg of ferrous sulfate 7H$_2$O was used in place of phosphomolybdic acid. The results are shown in Table 9 below.

TABLE 9

| Compara. Example | Conversion (%) | Yield (%) | Selectivity (%) |
| --- | --- | --- | --- |
| 2 | 70 | 9 | 13 |

What is claimed is:

1. A process for the preparation of 2,3-dimethoxy-5-methylbenzoquinone, comprising reacting 3,4,5-trimethoxytoluene with hydrogen peroxide, at a temperature of 100° C. or less, in the presence of a heteropolyacid selected from the group consisting of phosphomolybdic acids, phosphotungstic acids, silicomolybdic acids, silicotungstic acids and ammonium and alkali metal salts thereof.

2. A process as set forth in claim 1, wherein said reaction is performed using a water-soluble organic solvent.

3. A process as set forth in claim 2, wherein said solvent is formic acid, acetic acid, acetic anhydride, propionic acid, acetonitrile, methanol, ethanol, acetone or N,N-dimethylformamide.

4. A process as set forth in claim 1, wherein the amount of the hydrogen peroxide is 1–30 times the stoichiometric amount.

5. A process as set forth in claim 4, wherein the amount of the hydrogen peroxide is 2–10 times the stoichiometric amount.

6. A process as set forth in claim 1, wherein the amount of the heteropolyacid is 0.0001 to 0.05 mole per mole of the 3,4,5-trimethoxytoluene.

7. A process as set forth in claim 6, wherein the amount of the heteropolyacid is 0.001 to 0.03 mole per mole of the 3,4,5-trimethoxytoluene.

8. A process as set forth in claim 1, wherein said reaction is carried out at a temperature of 0–100 ° C.

9. A process as set forth in claim 8, wherein said reaction is carried out at a temperature of 10–70 ° C.

10. A process as set forth in claim 1, wherein said reaction is carried out for 1–24 hours.

11. A process as set forth in claim 1, wherein said salt is an alkali metal salt.

* * * * *